(12) United States Patent
Jesse et al.

(10) Patent No.: US 7,491,934 B2
(45) Date of Patent: Feb. 17, 2009

(54) SEM TECHNIQUE FOR IMAGING AND MEASURING ELECTRONIC TRANSPORT IN NANOCOMPOSITES BASED ON ELECTRIC FIELD INDUCED CONTRAST

(75) Inventors: Stephen Jesse, Knoxville, TN (US); David B. Geohegan, Knoxville, TN (US); Michael Guillorn, Brooktondale, NY (US)

(73) Assignee: UT-Battelle, LLC, Oak Ridge, TN (US)

( * ) Notice: Subject to any disclaimer, the term of this patent is extended or adjusted under 35 U.S.C. 154(b) by 273 days.

(21) Appl. No.: 11/331,840

(22) Filed: Jan. 13, 2006

(65) Prior Publication Data

US 2007/0164218 A1    Jul. 19, 2007

(51) Int. Cl.
*G01N 23/00* (2006.01)

(52) U.S. Cl. .................. 250/310; 250/306; 250/307; 324/751

(58) Field of Classification Search .............. 250/310, 250/440.11, 307; 324/751
See application file for complete search history.

(56) References Cited

U.S. PATENT DOCUMENTS 7,244,932 B2 *   7/2007   Nakasuji et al. ............. 250/306

2001/0002697 A1 *   6/2001   Hiroi et al. .................. 250/310

* cited by examiner

*Primary Examiner*—Jack I Berman
*Assistant Examiner*—Andrew Smyth
(74) *Attorney, Agent, or Firm*—Joseph A. Marasco; Judson R. Hightower (57) ABSTRACT

Methods and apparatus are described for SEM imaging and measuring electronic transport in nanocomposites based on electric field induced contrast. A method includes mounting a sample onto a sample holder, the sample including a sample material; wire bonding leads from the sample holder onto the sample; placing the sample holder in a vacuum chamber of a scanning electron microscope; connecting leads from the sample holder to a power source located outside the vacuum chamber; controlling secondary electron emission from the sample by applying a predetermined voltage to the sample through the leads; and generating an image of the secondary electron emission from the sample. An apparatus includes a sample holder for a scanning electron microscope having an electrical interconnect and leads on top of the sample holder electrically connected to the electrical interconnect; a power source and a controller connected to the electrical interconnect for applying voltage to the sample holder to control the secondary electron emission from a sample mounted on the sample holder; and a computer coupled to a secondary electron detector to generate images of the secondary electron emission from the sample.

20 Claims, 9 Drawing Sheets

SEM TECHNIQUE FOR IMAGING AND MEASURING ELECTRONIC TRANSPORT IN NANOCOMPOSITES BASED ON ELECTRIC FIELD INDUCED CONTRAST

STATEMENT AS TO RIGHTS TO INVENTIONS MADE UNDER FEDERALLY-SPONSORED RESEARCH OR DEVELOPMENT

This invention was made with United States Government support under prime contract No. DE-AC05-00OR22725 to UT-Battelle, L.L.C. awarded by the Department of Energy. The Government has certain rights in this invention.

BACKGROUND INFORMATION

1. Field of the Invention

Embodiments of the invention relate generally to the field of scanning electron microscopy (SEM). More particularly, embodiments of the invention relate to SEM techniques for imaging and measuring electronic transport in nanocomposites based on electric field induced contrast.

2. Discussion of the Related Art

Many new materials and devices envisioned in the near future will be based on using relatively long and slender conductive structures with unique electronic properties. These structures, commonly referred to as nanotubes, nanofibers, or nanowires can be used as additives to bulk materials to enhance the properties of the bulk material or add valuable properties to the bulk material. Nanowires may also be used individually to form the basic building blocks for next generation transistors or electron emitters. In any of these cases, progress requires knowledge of electronic transport properties within and between these nanowires as well as their influence on the electronic properties of the bulk material in which they reside.

Determining the location and accessing electronic transport information through nanomaterial percolation networks is difficult due to their small size and their fragile nature. This problem is exacerbated in the case of nano-composites since direct access is inhibited by a surrounding matrix. Few tools currently exist that have the ability to reveal, in-situ, the distribution of electric potential throughout these regions on such a small scale. Recent advances in scanning probe techniques, such as scanning impedance microscopy (SIM), offer possibilities, but with some limitations. One problem inherent with SIM, as with nearly all other scanning probe techniques, is the probe itself. The shape and quality of the tip can profoundly influence measurements. Reliability becomes a problem since shape and quality can vary from tip to tip and can change during even a single scan due to frictional wear or contamination. In addition, a high quality scan can take several minutes to capture, and in this time, the sample can drift causing distortion in the final image. The process of scanning probe microscopy becomes somewhat of an art since the operator has to find a balance between scanning slowly in order to reduce noise and increase resolution, and scanning quickly enough to avoid image distortion and tip degradation. Also, even though SIM has been shown to be capable of imaging nanowires inside a composite, the remarkable resolution commonly associated with scanning probe techniques is greatly diminished by the presence of a polymer.

Surface bias imaging using an SEM is know to those of skill in the art of scanning electron microscopy, and it is commonly referred to as 'voltage contrast'. This term has come to encompass two main types of measurements. In using the terminology of Seiler, voltage contrast I is based on using sample biases on the order of 100's or 1000's volts to influence the trajectory of primary electrons. Such large voltages are not useful for measuring potential distributions in nanowires since the current flow associated with such high currents would destroy them. Voltage contrast II requires acquiring and measuring shifts in spectral energy distributions of secondary electrons and is not applicable for making maps of potential since the spectra are not taken locally. Voltage contrast II is instead useful only in measuring the average surface potential over the entire scan area in the SEM.

In summary, scanning probe measurements are slow, difficult to perform, plagued by reliability issues, and can not always provide sufficient resolution. Currently available SEM techniques can not offer adequate voltage and spatial resolution simultaneously.

SUMMARY OF THE INVENTION

There is a need for the following embodiments of the invention. Of course, the invention is not limited to these embodiments.

According to an embodiment of the invention, a process comprises: mounting a sample onto a sample holder, the sample including a sample material; wire bonding leads from the sample holder onto the sample; placing the sample holder in a vacuum chamber of a scanning electron microscope; connecting leads from the sample holder to a power source located outside the vacuum chamber; controlling secondary electron emission from the sample by applying a predetermined voltage to the sample through the leads; and generating an image of the secondary electron emission from the sample. According to another embodiment of the invention, a machine comprises: a sample holder for a scanning electron microscope having an electrical interconnect and leads on top of the sample holder electrically connected to the electrical interconnect; a power source and a controller connected to the electrical interconnect for applying voltage to the sample holder to control the secondary electron emission from a sample mounted on the sample holder; and a computer coupled to a secondary electron detector to generate images of the secondary electron emission from the sample.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of an embodiment of the invention without departing from the spirit thereof, and embodiments of the invention include all such substitutions, modifications, additions and/or rearrangements.

BRIEF DESCRIPTION OF THE DRAWINGS

The drawings accompanying and forming part of this specification are included to depict certain embodiments of the invention. A clearer conception of embodiments of the invention, and of the components combinable with, and operation of systems provided with, embodiments of the invention, will become more readily apparent by referring to the exemplary, and therefore nonlimiting, embodiments illustrated in the drawings, wherein identical reference numerals (if they occur in more than one view) designate the same elements. Embodiments of the invention may be better understood by reference to one or more of these drawings in combination with the description presented herein. It should be noted that the features illustrated in the drawings are not necessarily drawn to scale.

FIGS. 3a-3d are views of sample geometry where.

FIGS. 6a-6c are views of a test structure and experimental results where.

FIGS. 7a-7d are a series of voltage contrast SEM micrographs under various bias conditions where.

DESCRIPTION OF PREFERRED EMBODIMENTS

Embodiments of the invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the embodiments of the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Within this application several publications are referenced by Arabic numerals, or principal author's name followed by year of publication, within parentheses or brackets. Full citations for these, and other, publications may be found at the end of the specification immediately preceding the claims after the section heading References. The disclosures of all these publications in their entireties are hereby expressly incorporated by reference herein for the purpose of indicating the background of embodiments of the invention and illustrating the state of the art.

The invention can be used to locate, image, and measure electronic transport through conductive pathways in thin film nano-composite materials. It is a technique utilizing state of the art, high resolution SEM technology in which high electric fields can be induced through the sample in order to distinguish regions within a thin film that can carry current from those that are electrically insulating. Since this method uses an electron microscope, the resolution of the information gathered is on the order of that of the SEM. In addition, this invention includes a calibration process to correlate brightness to local potential so that the degree of local conductivity can be assessed quantitatively. In this technique, voltage is applied to the network through two or more electrodes while inside the SEM. Conductive pathways, which could be of the form of a percolation network of nanoparticles, nanowires, or nanotubes or some other additive, in contact with the electrodes acquire some of this applied potential. Since secondary electron emission and detection, which mediates brightness and contrast in the SEM, are functions of electronic band structure of the material being imaged, localized changes in bias and electric fields will affect the band structure and the apparent local brightness. Thus the apparatus and method of the present invention control the secondary electron emission from a sample by applying a voltage bias to the sample. The sample geometry is important to the functionality of this method and can be designed so that large electric fields are generated from relatively small applied biases. This is important since large voltages (and the subsequent current flows) can easily destroy such small percolation networks. This invention is particularly useful in the realm of plastic electronics in which it has been shown that the addition of nanomaterials greatly enhances overall properties. This technique can be used to assess, in-situ, the density, dispersion, and orientation of additives along with information about their role in enhancing electronic properties of the bulk.

Potential maps of a network can be generated by correlating measured changes in brightness in a series of SEM images to surface potential. The results of such measurement can show the voltage distribution throughout a nanoscale network, and from this it is possible to determine the conductivity of individual nanowires and the conductivity between two nanowires in contact with one another.

This technique utilizes a standard SEM, and can been implemented specifically, for example, in a Hitachi S4700 microscope. Control of voltages of electrodes is accomplished by connecting wires from the sample surface inside the SEM vacuum chamber to power sources outside the chamber. A custom sample holder was built to provide this functionality and to facilitate sample exchange. This sample holder fits into the same locking device as a standard sample holder, but has an additional electrical interconnect. Leads from the top of the sample holder are connected to one side of interconnect. The other end mates with a permanently mounted connector inside the SEM chamber. Wires from the permanent connector lead out of the vacuum chamber.

Figure 1:
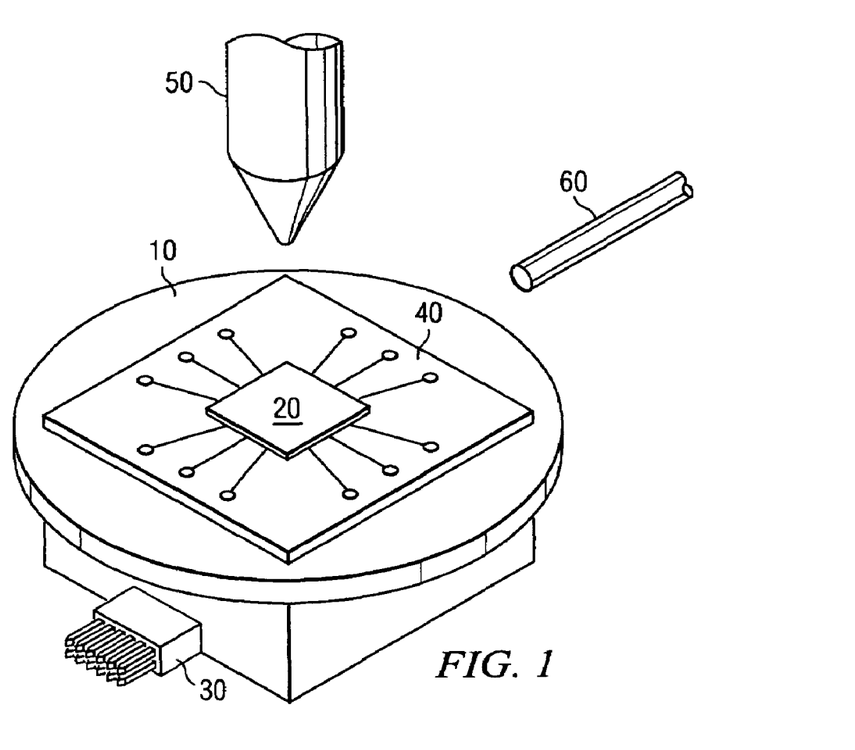
FIG. 1 is a schematic view of the apparatus of the invention.
Figure 2A:
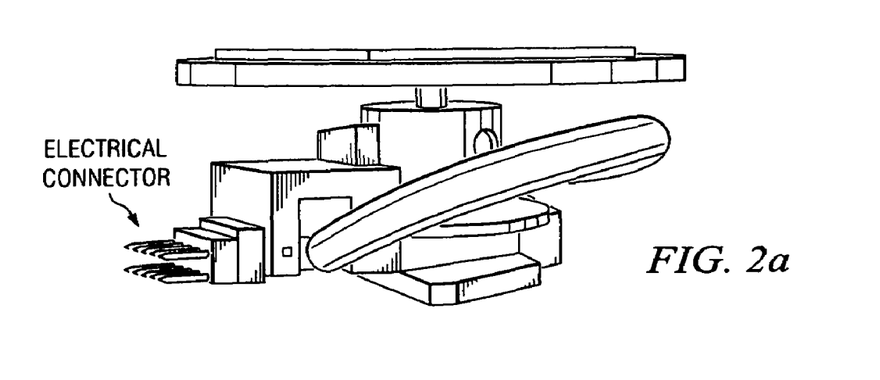
FIGS. 2a-2d are photograph views of a sample holder, representing an embodiment of the invention.
Figure 2B:
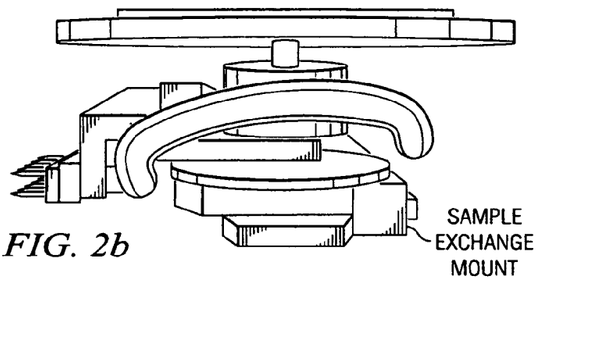
Figure 2C:
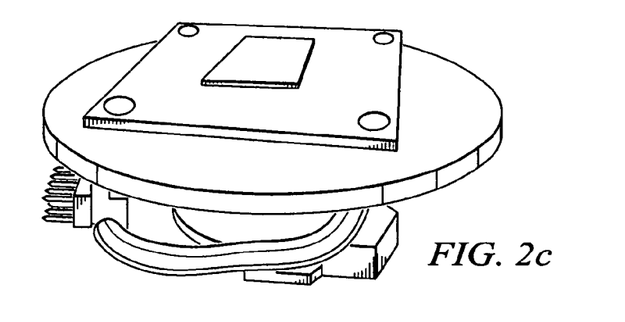
Figure 2D:
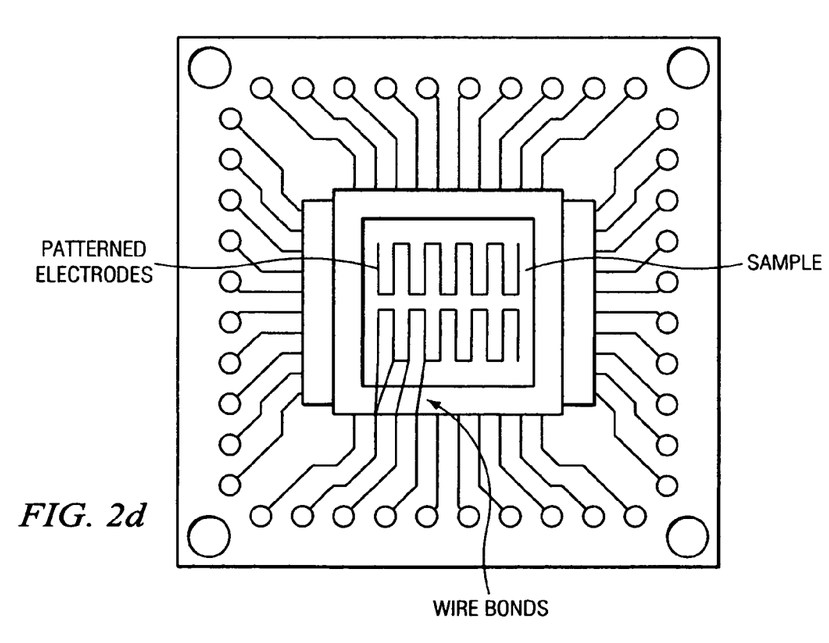

FIG. 1 illustrates a schematic drawing of the apparatus of the present invention. FIG. 1 represents the inside of a vacuum chamber of a standard SEM. The sample holder (10) has an interconnect (30) which connects to a power source and controller located outside the vacuum chamber. The interconnect provides an electrical connection to the leads (40)

located on top of the sample holder. Wire bonds from the leads lead to electrodes patterned on the sample (20), which is mounted on top of the sample holder (see FIG. 2d). The controller is used to apply voltage to the electrodes of the sample through the interconnect and the leads. The controller may be a computer or be connected to a computer. This computer may comprise a calibrating component or use a calibrating program to correlate brightness to local potential within the sample. Furthermore, the number of connections in the interconnect (30), and the leads (40) is sufficiently high to provide individual connection to all the electrodes of a sample through the wire bonds. The sample may contain a complex circuit with a large number of electrodes, and the number of connections in the interconnect must anticipate this. The controller has the capacity to selectively apply voltage to any selected set of electrodes to test any electrical pathway between any combination of electrodes within the sample.

An electron gun generates a beam of electrons focused by an objective lens (50) located above the sample. The interaction of the electron beam and the sample generates several different signals which are used for sample analysis. The most common generated signals utilized in a standard SEM include x-rays, primary backscattered electrons, and secondary electrons. The present invention makes use of the secondary electrons, which are detected by a secondary electron detector (60). Secondary electrons are electrons emitted from the sample through inelastic collisions with the beam electrons, generally with energy less than 50 eV. These secondary electrons primarily result from interaction between the high energy beam electrons and weakly-bonded electrons in the substrate. Due to the large energy difference between these electrons and the incident beam electrons, only a small amount of energy is transferred, resulting in inelastic collisions.

The detector (60) is generally a standard Everhart-Thornley (ET) detector, in which a scintillator material is struck by the secondary electrons emitted from the sample. This collision generates photons, which are reflected into a photomultiplier, and the resulting beam of light can pass through the vacuum environment through a quartz window, whereupon the photons are converted back into electrons which are then collected by a detector. The detector is coupled to equipment or circuitry which converts this data to an image of the sample, which is further connected to image collecting and storing equipment, such as a computer, which can further include image processing components or programs for combining different images. The equipment or circuitry may also be coupled to a mapping component, such as a computer, for generating a quantitative potential map of the sample from an image.

Figure 3A:
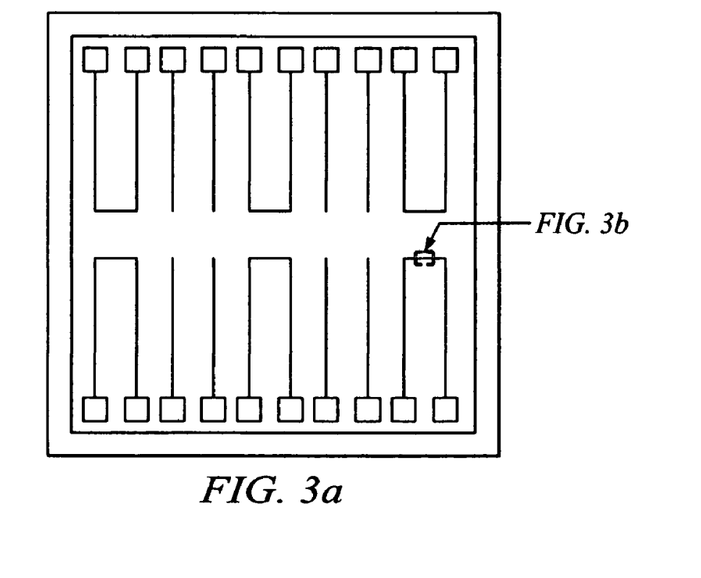
FIG. 3a is a plan view of electrode layout.

More detailed photographs of the sample mount are shown in FIGS. 2a-2d. Sample geometry is very important in enhancing the sensitivity of this technique to surface potentials. Standard micro-fabrication procedures are used in sample preparation. A silicon oxide film of 100 nm to 500 nm thickness is deposited or thermally grown onto silicon wafer. Photo-lithographically patterned electrodes of gold are then patterned on top of the oxide surface. The electrodes may be uniformly distributed along the sample, and aligned along two opposing edges as shown in FIG. 3a. A solution containing either nanotubes in a solvent, or nanotubes and polymer in a solvent is deposited onto the sample surface. The resulting sample has networks of nanotubes, either inside a polymer matrix or exposed (neat) on the oxide surface, connected to electrodes. The electrodes and nanotubes networks are separated from the silicon back gate by an insulating silicon oxide layer. The silicon wafer behaves much like the back-gate in planar transistors in that it can serve to generate large electric fields around biased elements on the sample surface.

Figure 3B:
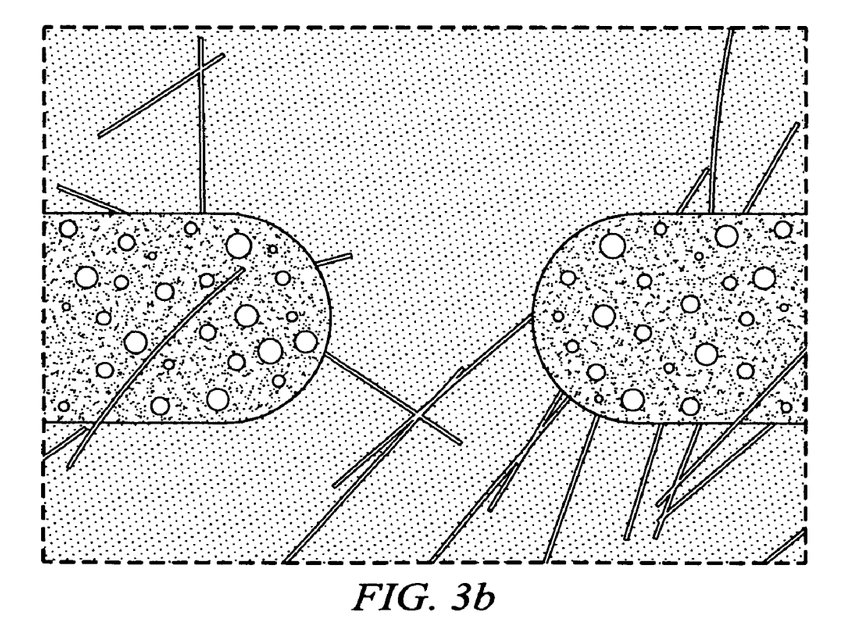
FIG. 3b is an SEM image of nanotube bundles in a thin film of polymer.
Figure 3C:
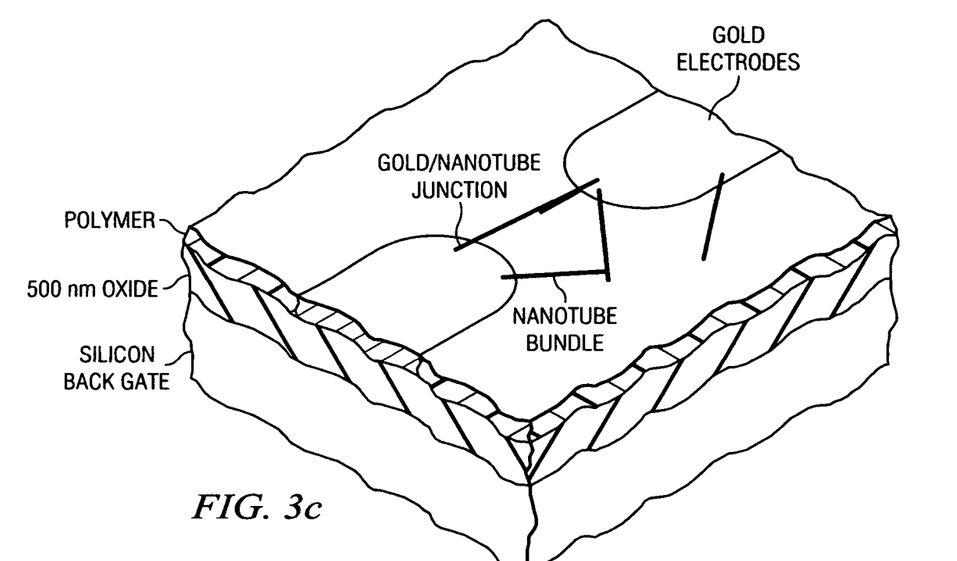
FIG. 3c is a schematic of a high magnification oblique view.
Figure 3D:
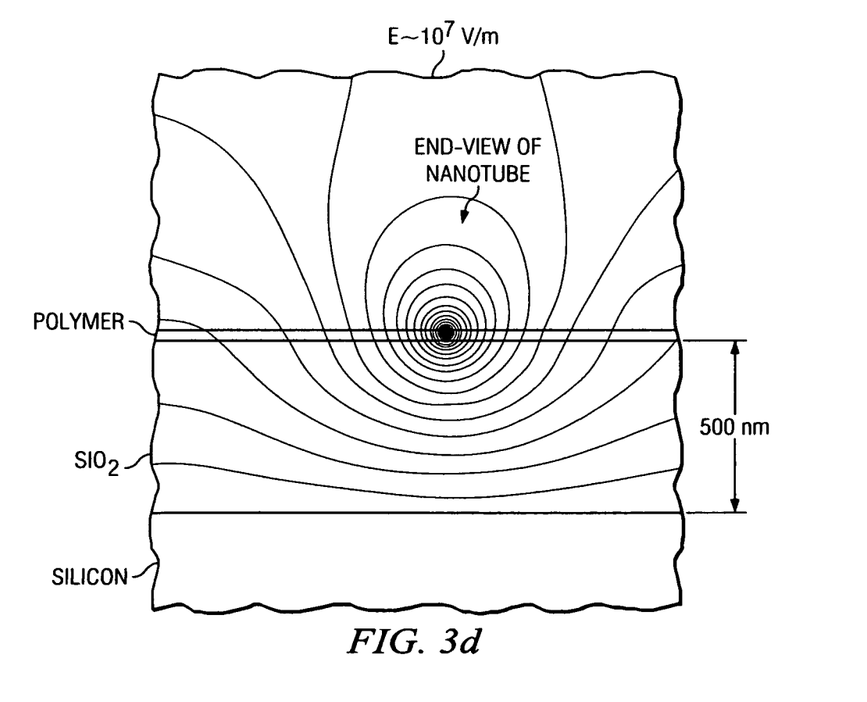
FIG. 3d is an end on view of a nanotube in polymer, separated from the back gate by an SiO2 layer (the lettered curves represent calculated lines of equipotential for the case when the nanotube is at a different potential than the back gate), representing embodiments of the invention.

FIGS. 3a-3d highlight some of the important aspects of the sample geometry through a series of different views of a typical substrate. FIG. 3a shows a low magnification view of a sample similar to that shown in FIG. 2d. FIG. 3b is an SEM image of nanotube bundles forming a network across two gold electrodes spaced 1 micron apart. FIG. 3c is a sketch of an oblique view, and FIG. 3d shows an end-on view of the nanotube. Lines of equipotential have been superimposed onto this image for the case where the nanotube bundle is at a different voltage than the silicon back gate. It is important to note that the very small radius of the nanotube along with its close proximity to the back gate result in an extremely high electric field near the surface of the nanotube. This field can be on the order of $10^7$ V/m for relatively small applied biases, such as on the order of a few volts. If there were no back gate, or if it was very far away, the electric field at the surface of the nanotube would not be as strong. As will be shown, the high fields resulting from this sample geometry play an important role in the increased sensitivity of this 'voltage contrast' technique over previous ones.

A sample can be placed on the sample stage with electrical leads wire bonded to the surface electrodes and inserted into the SEM. The voltage on the leads is controlled and sourced from outside the SEM. Focus and stigmation adjustments can be made in the operation of the SEM to generate a clear image of the network.

Figure 4A:
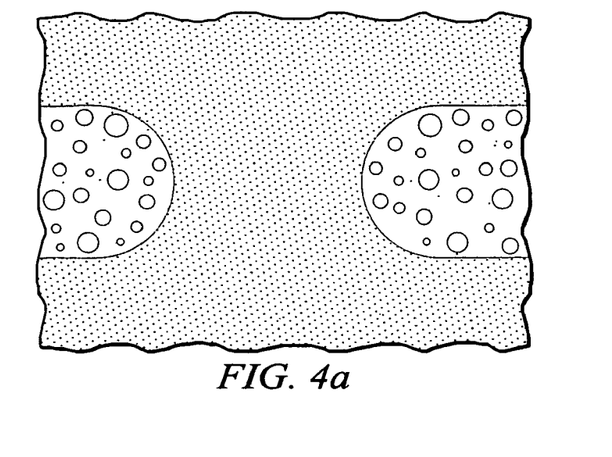
FIGS. 4a-4g are views of results of measuring the effects of applied bias in the SEM: equal bias was applied to both electrodes; (a-f) SEM images of SWNT bundles in PMMA with applied biases of (a) +5 V, (b) 0 V, (c) 5 V, (d) 10 V, (e) 15 V, (f) 20 V relative to the back gate, (g) plot of the normalized measured brightness of nanotube bundles as function of applied bias, representing an embodiment of the invention.
Figure 4B:
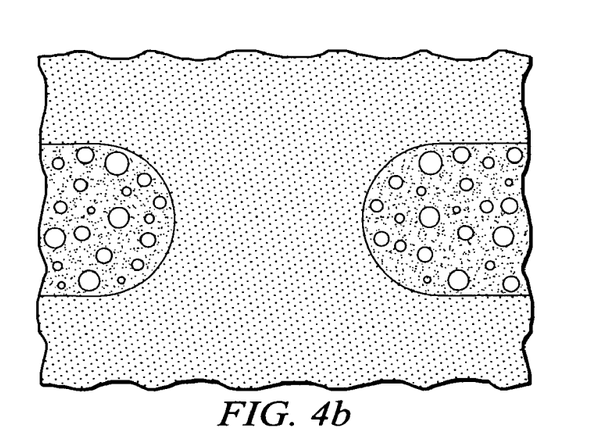
Figure 4C:
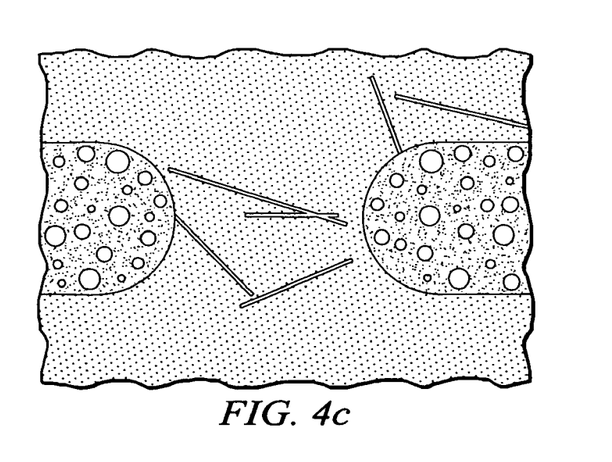
Figure 4D:
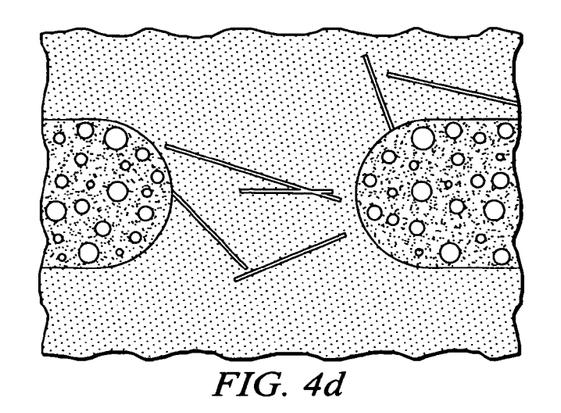
Figure 4E:
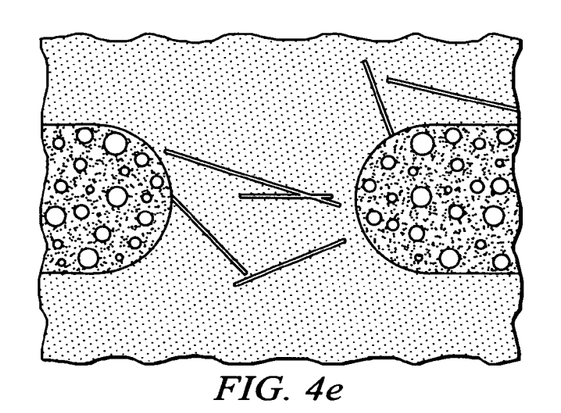
Figure 4F:
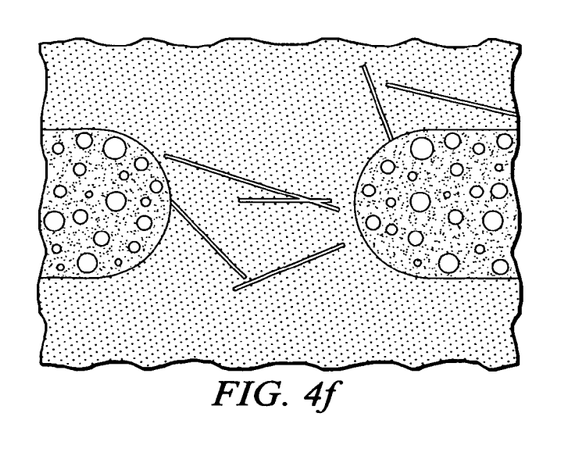

FIGS. 4a-4f show a series of SEM images taken over a range of applied biases. In each of these images, both electrodes were held at the same bias relative to one another, therefore, insuring that all connected nanotubes are at that same bias. This measurement is performed to collect information that will be used to calibrate brightness with surface potential. The applied voltage is measured relative to the silicon back gate held at the same potential as microscope ground. When bias is applied to the electrodes, a resulting change in brightness is observed in both nanotubes and the gold electrodes. In this series of images, the settings for brightness and contrast control were constant. FIG. 4a is the only image in this series for which a positive bias was applied. The electrodes are hardly visible and the nanotubes are indiscernible from the background. The nanotubes become faintly visible in FIG. 4f when ground to the back gate. Brightness of conductive regions steadily increases in FIGS. 4c-4d and reaches a maximum brightness at 15 V in FIG. 4e. A further increase in negative bias to −20 V results in a decrease in brightness as seen in FIG. 4f.

Figure 4G:
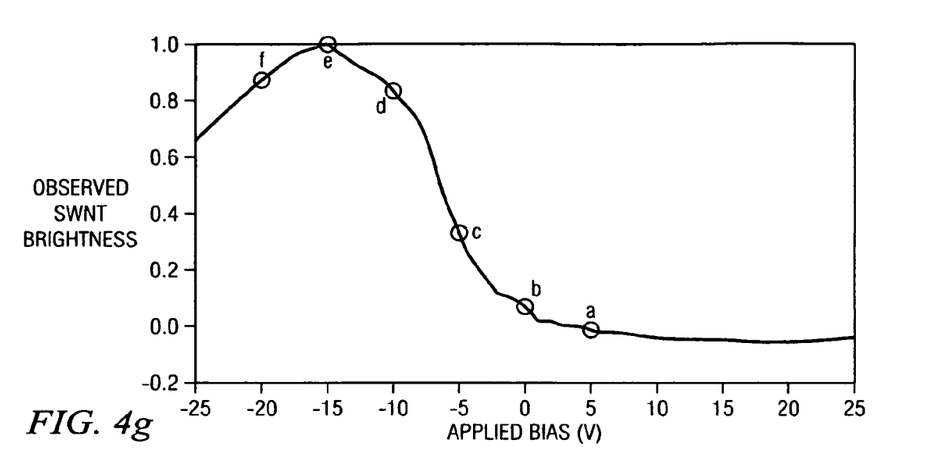

The voltage induced contrast result have been quantified by defining brightness as the difference in the value, as measured on an 8-bit scale, of a pixel and the average value of the background pixels. A computer program was written so that user defined boundaries indicate the pixels within the image corresponding to the nanotubes and those belonging to the background. The average brightness over all the nanotubes has been determined over a range of bias conditions and plotted in FIG. 4g. The units of brightness are arbitrary and the curve has been normalized relative to the condition for greatest brightness. The points on this curve corresponding to the images depicted in FIGS. 4a-4f are indicated in FIG. 4g. The curve in FIG. 4g is very useful in itself in that it provides a technique to relate pixel brightness to surface potential directly. With this information, one can generate a map of surface potential over a range of bias conditions from just SEM images.

Figure 5A:
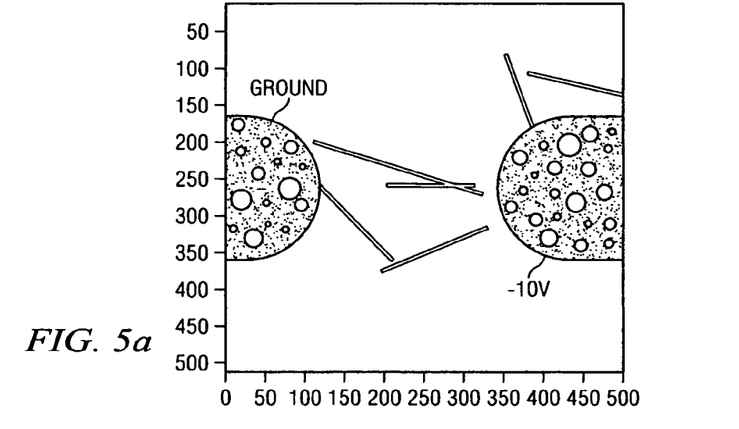
FIGS. 5a-5b are view of a measured potential map throughout a network of carbon nanotubes under two different bias conditions, representing an embodiment of the invention.
Figure 5B:
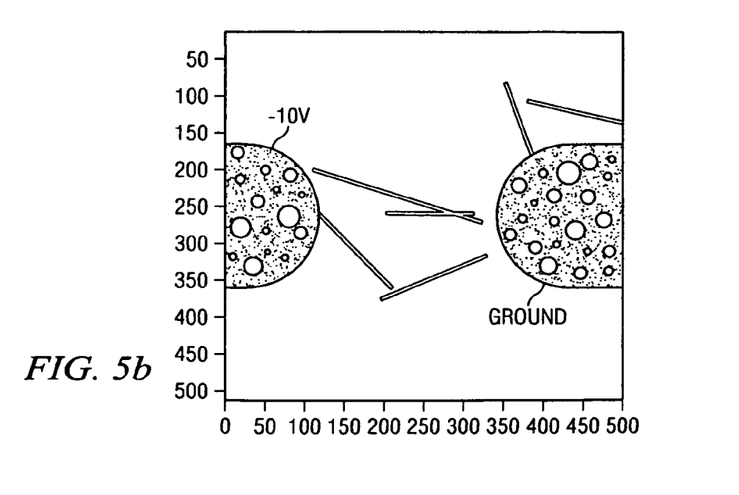

With a relationship between bias and brightness established, it is possible to calibrate SEM images and render maps of surface potential when a difference in potential is applied across the network. An example of this is shown in FIGS. 5a-5b. The background and most of the electrodes have been removed for clarity in FIGS. 5a-5b. Two bias conditions are shown. In FIG. 5a, the right electrode is −10 V and the left electrode is ground. In FIG. 5b, the opposite bias condition is shown.

EXAMPLE

A specific embodiment of the invention will now be further described by the following, nonlimiting example which will serve to illustrate in some detail various features. The following example is included to facilitate an understanding of ways in which an embodiment of the invention may be practiced. It should be appreciated that the example which follows represents embodiment discovered to function well in the practice of the invention, and thus can be considered to constitute preferred mode(s) for the practice of the embodiments of the invention. However, it should be appreciated that many changes can be made in the exemplary embodiment which is disclosed without departing from the spirit and scope of an embodiment of the invention. Accordingly, the example should not be construed as limiting the scope of the invention.

A new electric field-induced contrast mechanism for scanning electron microscopy is disclosed which permits the visualization of embedded nanomaterials inside various matrices with high-contrast and high-definition. The high contrast is proposed to result from localized enhancement of secondary electron emission from the nanomaterials due to electric field-induced changes in their work functions. By utilizing a stage that allows in situ current-voltage measurements inside a scanning electron microscope, single-walled carbon nanotubes (SWNTs) embedded within polymethyl methacrylate films were visualized directly. In addition to the rapid assessment of nanotube dispersion within polymers, electric-field induced contrast imaging enables the determination of percolation pathways. From the contrast in the images, the relative voltage at all points in the electron micrograph can be determined, providing a new mechanism to understand electronic percolation through nanoscale networks.

Carbon nanotubes are being explored as additives to lend both strength and useful electrical properties to polymers. While other conductive additives have fulfilled this role, the large aspect ratio of nanotubes require much smaller weight loadings to exceed percolation thresholds. Moreover, the unique electronic and optical properties intrinsic to single-walled carbon nanotubes (SWNTs) make them materials of choice for emerging applications requiring multifunctional polymer nanocomposites.

However, assessing dispersion of SWNT bundles inside polymers and analyzing the electrical properties of the percolation networks they form has been a major obstacle for both the fundamental understanding and the practical application of nanotube-polymer composites. Macroscale electrical measurements of bulk composites[1,2] and probabilistic estimations[3,4], though useful in determining percolation thresholds, are too blunt a tool to reveal the junction resistance between nanotube bundles and the electronic conduction pathways through the polymer which are responsible for the macroscopic properties. Bottom-up approaches, like first principle atomic scale modeling, could in theory render useful information for modeling nanotube bundle junctions in polymer composites as they have for single nanotube junctions[5-7]. However, similar calculations are yet intractable for bundle-bundle junctions given the large number of atoms participating in transport and current computation capacity.

The mechanism responsible for enhancing the secondary electron yield from biased nanomaterials will be described for the first time. It will be shown that it enables high-contrast, high-definition imaging of percolation networks in situ during current-voltage measurements within a scanning electron microscope. The experimental technique is specifically described for SWNT networks inside polymers. In addition, we describe the use of simple image processing used to indicate which nanotubes participate in current flow within the network. A simple model is presented to explain the remarkably high sensitivity of image brightness to surface potential. It will be shown that the surface potential generates very large electric fields in the vicinity of the high curvature surface of the nanotubes that form the conductive pathways. This field modulates the work function of the embedded nanomaterial, which in turn strongly affects its secondary electron emission yield, and is subsequently seen experimentally as a change in local brightness of the conductive pathway.

Nanotube-polymer composite films were prepared by spin casting purified (<0.01 wt. % metal), laser vaporization-grown, SWNT's[8,9] co-solubilized with poly-methyl methacrylate (PMMA) in ortho-dichlorobenzene (ODCB). A dispersed suspension of SWNTs in ODCB was prepared by 20 minutes of gentle sonication. ODCB provided the best dispersion of the highly-purified, strongly-bundled SWNTs used in these studies, and its relatively high boiling point was compatible with spin casting. PMMA/ODCB solutions were prepared separately, stored for several days to allow for the relatively slow solubilization to take place, and finally filtered with a 0.2-micron mesh polyvinylidene fluoride filter to remove any undissolved polymer. The composite solution was prepared by mixing solutions of SWNT/ODCB (weight loadings between 10-100 μg/g) and PMMA/ODCB (1.0-2.0 weight percent) together.

Composite solutions were spun cast onto lithographically pre-patterned gold electrode structures with minimum separation distances of 1-2 μm. The electrodes were separated from a silicon back gate by a 500 nm-thick $SiO_2$ layer. Spin casting of the very dilute solutions yielded SWNT/PMMA composite films that were 40-100 nm-thick with weight loadings between 0.1-1.0 wt %. The small film thickness was advantageous since the possible conductive pathways was reduced to essentially the two dimensions of the thin film. Hence, the complete topology of the conductive network could be determined from SEM micrographs.

High-resolution transmission electron microscope (HR-TEM) imaging was performed on composite films formed by spin casting SWNT/PMMA/ODCB solutions onto holey carbon grids. While individual SWNTs or small SWNT bundles were present, it was determined that nanotubes typically formed into bundles of 10-20 nm diameters.

'Voltage Contrast' (VC) is the term generally used to refer to the phenomenon by which a change in surface bias results in a change in brightness[12] as viewed in an SEM. This is a misleading description of what is occurring in the technique outlined here. The sensitivity of brightness to surface bias in this study far exceeds what would be expected by voltage contrast alone in which surface potentials need to be on the order of kilovolts in order to appreciably retard or accelerate high energy incident electrons. In our experiments, small biases (no larger than ±30V) resulted in significant contrast differences. The small surface voltage does however induce in a significant electric field ($10^7$-$10^8$V/m) between the conductive path formed by the electrodes and connected nanotubes on the top side of the sample and the silicon back gate beneath. This large electric field is primarily responsible for the image contrast. We therefore propose the term 'electric field induced contrast' (EFIC). VC depends on the affecting the primary electron (PE) beam with surface bias. EFIC effects are instead due to changes in secondary electron (SE) emission and detection per electric field induced modulation of material work function. Therefore the present method achieves a higher contrast by controlling the secondary electron emission from the sample through an applied voltage.

Large electric fields ($10^7$-$10^8$V/m) are generated between the conductive path and silicon back gate causing a shift in the effective work function of the conductive path. This subsequently changes the emission characteristics of biased regions and can be understood by considering the Schottky effect (eq. $1^{10}$), the spectrum of SE (eq. $2^{11}$), and the integrated intensity of SE (sometimes referred to as the 'S-curve') found by integrating eq. 2 over $E_s$ (eq. 3).

$$\Phi_{eff}(V_s) = \Phi - \sqrt{\frac{q^3}{4 \cdot \pi \cdot \varepsilon} E(V_s)} \qquad \text{Eq. 1}$$

$$\frac{d}{dE_s} N(E_s, \Phi_{eff}, E_F) = k \cdot \left| \frac{(E_s - E_F - \Phi_{eff})}{(E_s - E_F)^4} \right| \qquad \text{Eq. 2}$$

$$N(V_s) = \frac{k}{6} \cdot \frac{\Phi_{eff}(V_s) + 3 \cdot V_s}{(\Phi_{eff}(V_s) + V_s)^3} \qquad \text{Eq. 3}$$

Equation 1 shows how the effective work function ($\Phi_{eff}$) can be shifted from the material's actual work function ($\Phi$) in the presence of an electric field (E) where q is electron charge and $\in$ is the dielectric permittivity. The electric field is estimated by treating the nanotube bundle as the inner electrode of concentric capacitor plates as shown in equation 4, $$E(V_s) = \frac{V_s}{r_{nt} \cdot (\ln(d) - \ln(r_{nt}))} \qquad \text{Eq. 4}$$

where d is the oxide thickness, $r_{nt}$ bundle radius, and $V_s$ is the surface bias of the sample. This is an adequate approximation since we are concerned only with the electric field intensity at the surface of the nanotube. Equation 2 is the Chung-Everhart approximation of SE emission. $dN/dE_s$ is the number of secondary electrons emitted with the energy $E_s$. $E_F$ is the Fermi energy of the material and k is a relational constant. N is the total number of secondary electrons emitted.

Figure 6A:
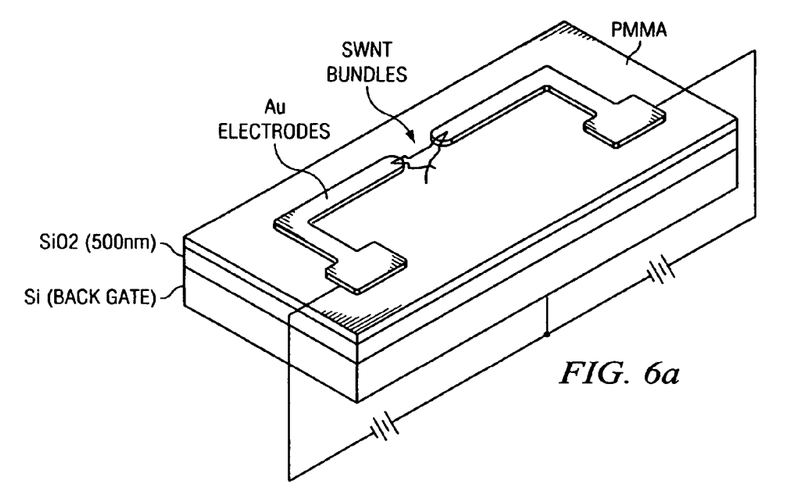
FIG. 6a is a schematic of the test structure.
Figure 6B:
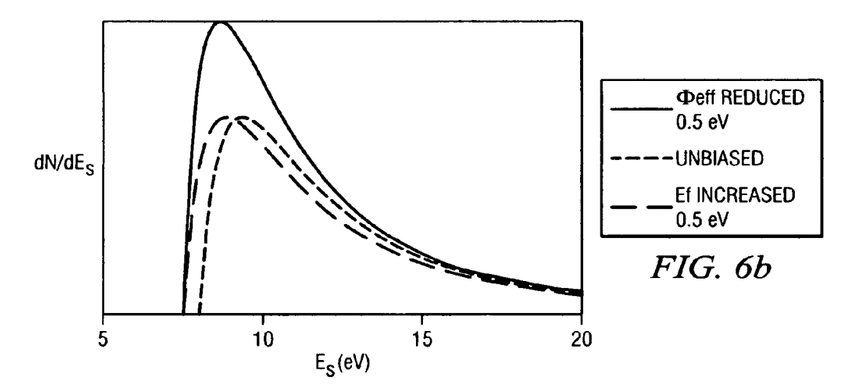
FIG. 6b are plots of equation 2 showing effects of shifting $\Phi_{eff}$ or $E_F$ on SE spectrum.
Figure 6C:
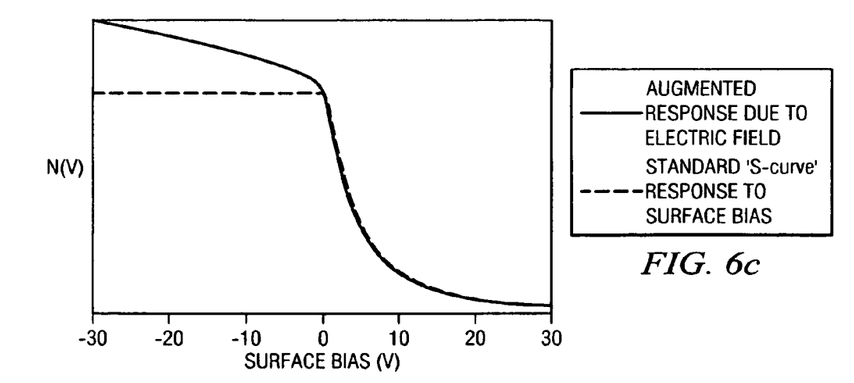
FIG. 6c shows integrated intensity of SE as a function of surface bias for a typical response where no appreciable electric field is present and the case where surface bias generates an intense electric field and provides an enhanced response (the surface bias axis in FIG. 6c is offset so that 0V on the axis corresponds to the Fermi energy of the sample), representing an embodiment of the invention.

FIG. 6b illustrates the roles that a material's Fermi energy and work function play in its SE emission. Considering bias alone (and not the electric field it generates) results only in a change of the Fermi level within a conductor. Applying a negative bias would have the effect of shifting the SE spectrum in energy to the right but would not change the shape of the spectrum or the electron emission efficiency. A large enough positive bias can reduce SE emission if the curve is pushed far enough to the left. This is the reason for the sharp drop-off in SE yield in FIG. 6c. However, if the surface bias also happens to generate a significant electric field, as is the case in this study, an appreciable effective change in the work function can occur and the total number of emitted electrons can be strongly enhanced by a relatively small bias. The consequence of this is made clear in FIG. 6c where the integrated intensity is plotted against surface bias. Where normally a varying negative surface bias has no effect on brightness, a negative bias which coincidentally generates a strong electric field can.

The high sensitivity of image brightness to surface potential permits a simple means by which to map surface potential of biased samples. In order to further investigate how charging of the SWNTs in the polymer might be used to reveal characteristics of the nanotube networks, bias was applied to the network, revealing the nanotube networks and their connective paths.

Eq. 3 can be used to control secondary electron emission from the sample. Given a certain sample, it can be determined what voltage is required to generate an image with a requisite brightness. During the calibration procedure, for example, N can be calculated for each applied voltage and correlated with a certain brightness value, and this can further be used to determine the voltage required for that brightness. Or the approximate desired voltage for a given sample material with a know permittivity $\in$ can be determined. Alternately, V can be determined for a given a sample with a known approximate insulator material thickness or known bundle radius. One skilled in the art would know how to implement any of these equations and methods into a computerized process.

FIGS. 7a-7d show SEM micrographs of the Au electrodes separated by 2 μm in a 0.3 weight percent SWNT/PMMA composite film. When small negative biases (−20V) are applied to both electrodes (as in FIG. 7a), all the nanotubes in contact with both electrodes, or well-contacted by these nanotubes, appear brightly in the image. Toward the periphery of the network, marginally-connected nanotubes display less contrast.

Figure 7A:
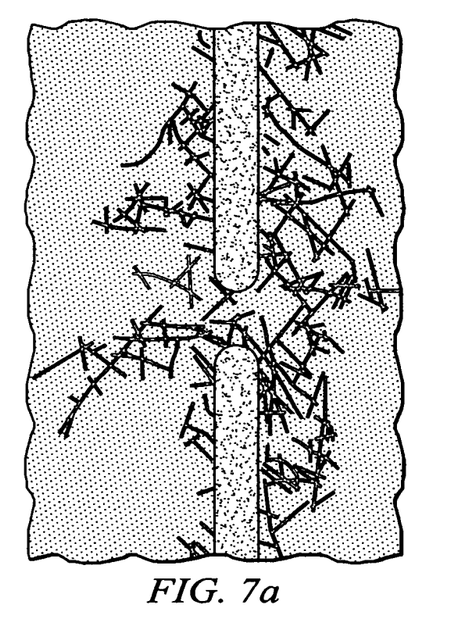
FIG. 7a shows both electrodes at −20V.
Figure 7B:
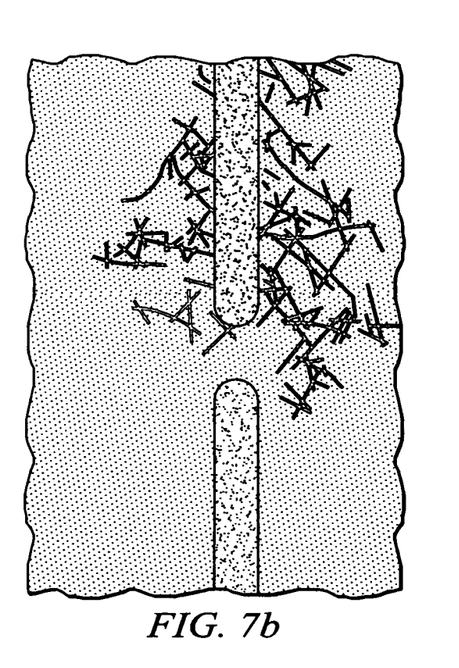
FIG. 7b shows the top electrode at −20V and the bottom electrode at ground.
Figure 7C:
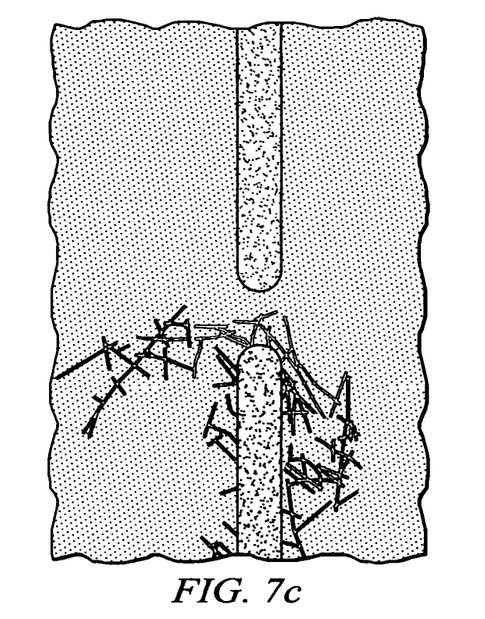
FIG. 7c shows the top electrode at ground and the bottom electrode at −20V.
Figure 7D:
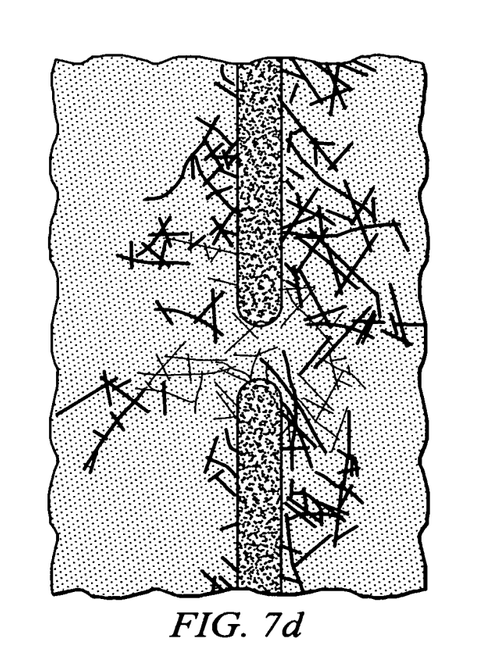
FIG. 7d shows an image generated by subtracting FIG. 7b and FIG. 7c from FIG. 7a, representing an embodiment of the invention.

In order to understand which nanotubes within the network participate in conduction between the two electrodes, one electrode was biased while the other was grounded. As shown in FIG. 7b, nanotubes connected only to the top electrode (biased at −20V) appear bright while nanotubes well connected to the grounded electrode are not visible. Nanotubes in shared contact with both electrodes are at an intermediate potential and therefore exhibit an intermediate brightness. FIG. 7c shows the reverse situation, with the top electrode at ground and the bottom electrode at −20V. By subtracting FIGS. 7b and 7c from FIG. 7a, the portions of the nanotube network in shared contact with both electrodes are brought into prominence, as shown in FIG. 7d. Extraneous nanotubes, which show up strongly in FIGS. 7b and 7c are eliminated from FIG. 7a. This simple image processing procedure demonstrates that qualitative potential maps of nanotubes imbedded in polymer can be measured and that nanotubes participating in current flow can be distinguished from merely attached to one or the other electrode. For a sample with a given electric circuit, the above technique may be repeated for different pairs of electrodes or for any chosen sets of electrodes.

This technique can be extended to provide a quantitative potential map throughout the circuit once spectral information about the secondary electron emission is measured. The outlined procedure quickly establishes which nanotubes participate in electrical transport as well as their relative degree of participation. Thus any conductive pathway between any two electrodes within a circuit can be analyzed in this way by providing a voltage bias between the two electrodes and obtaining a first image, and then alternately holding one electrode at ground while the other is under bias and this way obtaining second and third images, and subtracting the second and third images from the first image.

The electric field $E(V_s)$ given in Eq. 1 can be calculated for at any location of the sample represented by a pixel of the image by quantifying the brightness of pixel with the value of N in Eq. 3. Such a correlation can, for example, be obtained through the calibration process described earlier and shown in FIG. 4g. Thus a map of the electric field can be obtained from an image such as shown in FIGS. 7a-7d. One skilled in the art will know how to implement any of these equations and methods into a computerized process.

In summary, electric field-induced contrast (EFIC) is reported as a new contrast mechanism in scanning electron microscopy. Local changes in secondary electron yield resulting from field-induced changes in the work function are modeled to explain the high-contrast observed for electrically biased SWNTs inside PMMA observed during current-voltage measurements of nanotube-polymer composite films in situ within an SEM. Experimentally, EFIC SEM-imaging provides a valuable tool to assess dispersion of carbon nanotubes or other nanomaterials within polymers or other matrices and obtain a great deal of information about their electrical conductivity from the contrast in the images. It is possible with this technique to generate voltage potential maps across quasi-2D nanotube percolation networks embedded in thin polymer films, determine the local resistivity in nanotubes, and importantly, determine the junction resistance between nanotubes. EFIC imaging complements scanning probe based techniques[12] and is effective on the length scales where percolation theory breaks down from the loss of statistical significance but that are still too large for atomic scale transport computer simulations to be tractable. Visually mapping the potentials for real networks may be the first step to determine important constants for percolation theory estimates as well as establish bounds for atomic level simulations.

Practical Applications

A practical application of an embodiment of the invention that has value within the technological arts is as a research technique in the context of SEM research on nanoscale conductive structures. The invention is particularly well suited for studying nanocomposites and useful in studying plastic electronics. Since most plastic electronic devices are likely to have thin film architecture, in-situ observation of devices under operations would not be inhibited with the invention. The invention can be used to assess, in-situ, the density, dispersion and orientation of additives along with information about their role in enhancing electronic properties of the host material. It has been shown that the efficiency of polymer based solar cells and light emitters is enhanced by the addition of carbon nanotubes or nanorods of various materials. However, the exact role these additives play is still not well understood, and consequently the steps needed to optimize such a device are also unknown. This invention can facilitate basic science research into such potentially important devices. In addition, the invention is useful in monitoring large scale manufacturing. This invention is a relative high speed technique and could be incorporated in an assembly line to measure additive dispersion, orientation, and percolation network viability to ensure product quality. There are virtually innumerable uses for an embodiment of the invention, all of which need not be detailed here.

Definitions

The term program and/or the phrase computer program are intended to mean a sequence of instructions designed for execution on a computer system (e.g., a program and/or computer program, may include a subroutine, a function, a procedure, an object method, an object implementation, an executable application, an applet, a servlet, a source code, an object code, a shared library/dynamic load library and/or other sequence of instructions designed for execution on a computer or computer system). The phrase radio frequency is intended to mean frequencies less than or equal to approximately 300 GHz as well as the infrared spectrum. Group numbers corresponding to columns within the periodic table of the elements use the "New Notation" convention as seen in the CRC Handbook of Chemistry and Physics, 81$^{st}$ Edition (2000).

The term substantially is intended to mean largely but not necessarily wholly that which is specified. The term approximately is intended to mean at least close to a given value (e.g., within 10% of). The term generally is intended to mean at least approaching a given state. The term coupled is intended to mean connected, although not necessarily directly, and not necessarily mechanically. The term proximate, as used herein, is intended to mean close, near adjacent and/or coincident; and includes spatial situations where specified functions and/or results (if any) can be carried out and/or achieved. The term deploying is intended to mean designing, building, shipping, installing and/or operating.

The terms first or one, and the phrases at least a first or at least one, are intended to mean the singular or the plural unless it is clear from the intrinsic text of this document that it is meant otherwise. The terms second or another, and the phrases at least a second or at least another, are intended to mean the singular or the plural unless it is clear from the intrinsic text of this document that it is meant otherwise. Unless expressly stated to the contrary in the intrinsic text of this document, the term or is intended to mean an inclusive or and not an exclusive or. Specifically, a condition A or B is satisfied by any one of the following: A is true (or present) and B is false (or not present), A is false (or not present) and B is true (or present), and both A and B are true (or present). The terms a or an are employed for grammatical style and merely for convenience.

The term plurality is intended to mean two or more than two. The term any is intended to mean all applicable members of a set or at least a subset of all applicable members of the set. The phrase any integer derivable therein is intended to mean an integer between the corresponding numbers recited in the specification. The phrase any range derivable therein is intended to mean any range within such corresponding numbers. The term means, when followed by the term "for" is intended to mean hardware, firmware and/or software for achieving a result. The term step, when followed by the term "for" is intended to mean a (sub)method, (sub)process and/or (sub)routine for achieving the recited result.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. The terms "consisting" (consists, consisted) and/or "composing" (composes, composed) are intended to mean closed language that does not leave the recited method, apparatus or composition to the inclusion of procedures, structure(s) and/or ingredient(s) other than those recited except for ancillaries, adjuncts and/or impurities ordinarily associated therewith. The recital of the term "essentially" along with the term "consisting" (consists, consisted) and/or "composing" (composes, composed), is intended to mean modified close language that leaves the recited method, apparatus and/or composition open only for the inclusion of unspecified procedure(s), structure(s) and/or ingredient(s) which do not materially affect the basic novel characteristics of the recited method, apparatus and/or composition.

Unless otherwise defined, all technical and scientific terms used herein have the same meaning as commonly understood by one of ordinary skill in the art to which this invention belongs. In case of conflict, the present specification, including definitions, will control.

CONCLUSION

The described embodiments and examples are illustrative only and not intended to be limiting. Although embodiments of the invention can be implemented separately, embodiments of the invention may be integrated into the system(s) with which they are associated. All the embodiments of the invention disclosed herein can be made and used without undue experimentation in light of the disclosure. Although the best mode of the invention contemplated by the inventor(s) is disclosed, embodiments of the invention are not limited thereto. Embodiments of the invention are not limited by theoretical statements (if any) recited herein. The individual steps of embodiments of the invention need not be performed in the disclosed manner, or combined in the disclosed sequences, but may be performed in any and all manner and/or combined in any and all sequences. The individual components of embodiments of the invention need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials. Homologous replacements may be substituted for the substances described herein. Agents which are both chemically and physiologically related may be substituted for the agents described herein where the same or similar results would be achieved.

It can be appreciated by those of ordinary skill in the art to which embodiments of the invention pertain that various substitutions, modifications, additions and/or rearrangements of the features of embodiments of the invention may be made without deviating from the spirit and/or scope of the underlying inventive concept. All the disclosed elements and features of each disclosed embodiment can be combined with, or substituted for, the disclosed elements and features of every other disclosed embodiment except where such elements or features are mutually exclusive. The spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

REFERENCES (1) Blanchet, G. B.; Fincher, C. R.; Gao, F. *Appl. Phys. Lett.* 2003, 82,1290-1292.
(2) Kaiser, A. B.; Dusberg, G.; Roth, S. *Phys. Rev. B* 1998, 57,1418-1421.
(3) Balberg, I.; Binenbaum, N. *Phys. Rev. B* 1983, 28, 3799-3812.
(4) Balberg, I.; Binenbaum, N.; Wagner, N. *Phys. Rev. Lett.* 1984, 52,1465-1468.
(5) Buldum, A.; Lu, J. P. *Phys. Rev. B* 2001, 6316.
(6) Fuhrer, M. S.; Nygard, J.; Shih, L.; Forero, M.; Yoon, Y. G.; Mazzoni, M. S. C.; Choi, H. J.; Ihm, J.; Louie, S. G.; Zettl, A.; McEuen, P. L. *Science* 2000, 288, 494-497.
(7) Yoon, Y. G.; Mazzoni, M. S. C.; Choi, H. J.; Ihm, J.; Louie, S. G. *Phys. Rev. Lett.* 2001, 86, 688-691.
(8) Geohegan, D. B.; Schittenheim, H.; Fan, X.; Pennycook, S. J.; Puretzky, A. A.; Guillorn, M. A.; Blom, D. A.; Joy, D. C. *Appl. Phys. Lett.* 2001, 78, 3307-3309.
(9) Britt, P. F.; Viswanathan, S.; lvanov, I. N.; Puretzky, A. A.; Lance, M. J.; Geohegan, D. B. In *American Physical Society March Meeting*: Austin, TX, 2003.
(10) Kasap, S. O. *Principles of Electronic Materials and Devices*; 2nd edition ed.; McGraw-Hill Science/Engineering/Math: New York, 2001.
(11) Chung, M. S.; Everhart, T. E. *J Appl. Phys.* 1974, 45, 707-709.
(12) Kalinin, S. V.; Jesse, S.; Shin, J.; Baddorf, A. P.; Guillorn, M. A.; Geohegan, D. B. *Nanotechnology* 2004, 15, 907-912.
(13) Seiler, H., Secondary-Electron Emission in the Scanning Electron-Microscope; Journal of Applied Physics, 1983, 54(11), pages R1 -R18.

What is claimed is:

1. An apparatus comprising:
a sample holder for a scanning electron microscope having an electrical interconnect and leads on top of the sample holder electrically connected to the electrical interconnect, the sample mounted on the sample holder comprising a plurality of electrodes, the sample holder comprising wire bonds connecting the leads to the plurality of electrodes;
a power source and a controller connected to the electrical interconnect for applying voltage to the sample holder to control the secondary electron emission from a sample mounted on the sample holder; and
a computer coupled to a secondary electron detector to generate images of the secondary electron emission from the sample.

2. The apparatus of claim 1, wherein the computer comprises a calibrating component to calibrate the brightness of the images of the secondary electron emission from the sample by controlling the voltage applied to the sample holder.

3. The apparatus of claim 1, wherein the plurality of electrodes includes at least three electrodes and the controller applies voltage to one or more of at least two sets of electrodes selected from the plurality of electrodes.

4. The apparatus of claim 3, further comprising:
an image processing component for combining a plurality of images of the secondary electron emission from the sample; and
a mapping component for generating a quantitative potential map of the sample.

5. The apparatus of claim 1, wherein the sample comprises a sample material, said sample material having an original work function, and wherein the controller sets the voltage based on a predetermined desired secondary electron emission from the sample based on the equation:

$$N(V_s) = \frac{k}{6} \cdot \frac{\Phi_{eff}(V_s) + 3 \cdot V_s}{(\Phi_{eff}(V_s) + V_s)3}$$

where $N(V_s)$ is the number of secondary electrons emitted, V.sub.s is the voltage, k is a predetermined relational constant, and .PHI..sub.eff is an effective work function, determined by:

$$\Phi_{eff}(V_s) = \Phi - \sqrt{\frac{q^3}{4\cdot\pi\cdot\varepsilon} \cdot E(V_s)}$$

where $\Phi$ is the original work function, q is the electron charge, and $E(V_s)$ is the estimated electric field within the sample material.

6. The apparatus of claim 1, wherein the sample comprises:
a substrate;
an insulating layer;
a plurality of patterned electrodes; and
a network of nanotubes, either exposed or within a polymer matrix, located on top of the insulating layer.

7. The apparatus of claim 6, wherein the substrate comprises silicon, the insulating layer comprises silicon oxide, and the plurality of patterned electrodes comprise gold.

8. The apparatus of claim 6, wherein the plurality of patterned electrodes are uniformly distributed on the substrate and aligned along two opposing edges of the substrate.

9. A method comprising:
mounting a sample onto a sample holder, the sample including a sample material;
wire bonding leads from the sample holder onto the sample;
placing the sample holder in a vacuum chamber of a scanning electron microscope;
connecting leads from the sample holder to a power source located outside the vacuum chamber;
controlling secondary electron emission from the sample by applying a predetermined voltage to the sample through the leads; and
generating an image of the secondary electron emission from the sample.

10. The method of claim 9, further comprising generating a quantitative potential map of an electric circuit defined by the sample, the electric circuit including a plurality of electrodes, by selectively applying a voltage bias to one or more of at least two sets of electrodes selected from the plurality of electrodes.

11. The method of claim 9, further comprising, prior to generating an image, calibrating the predetermined voltage to effect maximum brightness of conductive pathways within the sample.

12. The method of claim 11, wherein calibrating includes:
selecting a series of voltages over a specified voltage range;
applying a voltage from the series of voltages;
generating an image while said voltage is applied;
determining which pixels of the image represent conductive pathways within the sample;
quantifying the brightness of the image by comparing a value of each pixel of each conductive pathway to a calculated average value of background pixels.

13. The method of claim 12, further comprising
applying another voltage from the series of voltages;
generating an image while said another voltage is applied;
determining which pixels of the image represent conductive pathways within the sample;
quantifying the brightness of the image by comparing the value of each pixel of each conductive pathway to a calculated average value of background pixels;
generating a curve of brightness as a function of voltage;
determining a maximum of the curve of brightness; and
applying a maximum voltage corresponding to the maximum of the curve of brightness.

14. The method of claim 9, wherein the sample material has an original work function and wherein the secondary electron emission from the sample is controlled by the predetermined voltage V.sub.s using the equation:

$$N(V_s) = \frac{k}{6} \cdot \frac{\Phi_{eff}(V_s) + 3\cdot V_s}{(\Phi_{eff}(V_s) + V_s)3}$$

where $N(V_s)$ is the number of secondary electrons emitted, k is a predetermined relational constant, and $\Phi_{eff}$ is the effective work function of the sample material, determined by:

$$\Phi_{eff}(V_s) = \Phi - \sqrt{\frac{q^3}{4\cdot\pi\cdot\varepsilon} \cdot E(V_s)}$$

where $\Phi$ is the original work function of the sample material, q is the electron charge, and $E(V_s)$ is the estimated electric field within the sample material.

15. The method of claim 9, further comprising calculating the electric field $E(V_s)$ at any pixel of the image of the secondary electron emission from the sample using the equation:

$$N(V_s) = \frac{k}{6} \cdot \frac{\Phi_{eff}(V_s) + 3\cdot V_s}{(\Phi_{eff}(V_s) + V_s)3}$$

where $N(V_s)$ is the number of secondary electrons emitted, determined from the brightness of said pixel, k is a predetermined relational constant, and $\Phi_{eff}$ is the effective work function of the sample material, determined by:

$$\Phi_{eff}(V_s) = \Phi - \sqrt{\frac{q^3}{4\cdot\pi\cdot\varepsilon} \cdot E(V_s)}$$

where $\Phi$ is the original work function of the sample material, and q is the electron charge.

16. The method of claim 9, wherein the sample includes an electrical circuit including a plurality of electrodes and further comprising:
a first step of selecting a first and second set of electrodes from the plurality of electrodes;
a second step of generating a first image of secondary electron emission from the sample while applying a negative voltage bias to both sets of electrodes;
a third step of generating a second image of secondary electron emission from the sample while applying a negative voltage bias to the first set of electrodes while keeping the second set of electrodes at ground;
a fourth step of generating a third image of the secondary electron emission from the sample while applying a negative voltage bias to the second set of electrodes while keeping the first set of electrodes at ground; and
a fifth step of generating a fourth image by subtracting the second and third images from the first image.

17. The method of claim 16, further comprising repeating the first step through the fifth step for a list of selected first and second sets of electrodes, thereby generating a quantitative potential map of the circuit.

18. The method of claim 17, further comprising:
for each first and second set of electrodes, calculating the electric field $E(V_s)$ at any desired pixel of the fifth image corresponding to said first and second set of electrodes, using the equation:

$$N(V_s) = \frac{k}{6} \cdot \frac{\Phi_{eff}(V_s) + 3 \cdot V_s}{(\Phi_{eff}(V_s) + V_s)3}$$

where $N(V_s)$ is the number of secondary electrons emitted, determined from the brightness of said pixel, k is a predetermined relational constant, and $\Phi_{eff}$ is the effective work function of the sample material, determined by:

$$\Phi_{eff}(V_s) = \Phi - \sqrt{\frac{q^3}{4 \cdot \pi \cdot \varepsilon} \cdot E(V_s)}$$

where $\Phi$ is the original work function of the sample material, and q is the electron charge.

19. The method of claim 9, wherein the sample is prepared by a method comprising:
providing a substrate;
depositing an insulating layer;
patterning electrodes on top of the insulating layer using photolithography;
depositing a solution containing either nanotubes in a solvent or nanotubes and polymer in a solvent on the surface of the insulating layer; and
evaporating the solvent.

20. An apparatus comprising:
a sample holder for a scanning electron microscope having an electrical interconnect and leads on top of the sample holder electrically connected to the electrical interconnect;
a power source and a controller connected to the electrical interconnect for applying voltage to the sample holder to control the secondary electron emission from a sample comprising a sample material, said sample mounted on the sample holder and said sample material having an original work function, wherein the controller sets the voltage based on a predetermined desired secondary electron emission from the sample based on the equation $$N(V_s) = \frac{k}{6} \cdot \frac{\phi_{eff}(V_s) + 3 \cdot V_s}{(\phi_{eff}(V_s) + V_s)3}$$

where N is the number of secondary electrons emitted, $V_s$ is the voltage, k is a predetermined relational constant, and $\Phi_{eff}$ is an effective work function of the sample material, determined by $$\phi_{eff}(V_s) = \phi - \sqrt{\frac{q^3}{4 \cdot \pi \cdot \varepsilon} \cdot E(V_s)}$$

where $\Phi$ is the original work function, q is the electron charge, and $E(V_s)$ is the estimated electric field within the sample material;
a computer coupled to a secondary electron detector to generate images of the secondary electron emission from the sample;
a calibrating component to calibrate the brightness of the images of the secondary electron emission from the sample by controlling the voltage applied to the sample holder;
an image processing component for combining a plurality of images of the secondary electron emission from the sample; and
a mapping component for generating a quantitative potential map of the sample,
wherein the sample includes
a substrate;
an insulating layer;
a plurality of patterned electrodes;
a network of nanotubes, either exposed or within a polymer matrix, on top of the insulating layer; and
wire bonds connecting the leads to the plurality of patterned electrodes.

* * * * *